United States Patent [19]  [11]  4,179,439
Sauciuc et al.  [45]  Dec. 18, 1979

[54] RIFAMYCINS AND METHOD FOR THEIR PREPARATION

[75] Inventors: Alexandru Sauciuc, Iaşi; Ion Nitelea; Eugeniu Paunescu, both of Bucharest; Constantin Diaconescu, Iaşi; Margareta Albu, Iaşi; Liliana Bulgaru, Iaşi; Eugen Diaconu, Iaşi, all of Romania

[73] Assignee: Intreprindera de Antibiotice Iaşi, Iaşi, Romania

[21] Appl. No.: 812,429

[22] Filed: Jul. 1, 1977

[51] Int. Cl.$^2$ .......................................... C07D 498/08
[52] U.S. Cl. .......................... 260/239.3 P; 424/250
[58] Field of Search .................................. 260/239.3 P

[56]  References Cited
U.S. PATENT DOCUMENTS

| | | | |
|---|---|---|---|
| 3,342,810 | 9/1967 | Maggi et al. | 260/239.3 P |
| 3,862,934 | 1/1975 | Cricchio et al. | 260/239.3 P |
| 3,865,812 | 2/1975 | Cricchio et al. | 260/239.3 P |
| 3,933,800 | 1/1976 | Cricchio et al. | 260/239.3 P |
| 3,963,705 | 6/1976 | Marsili et al. | 260/239.3 P |
| 4,005,076 | 1/1977 | Cricchio et al. | 260/239.3 P |

Primary Examiner—John M. Ford
Assistant Examiner—Robert T. Bond
Attorney, Agent, or Firm—Karl F. Ross

[57]  ABSTRACT

The invention is concerned to new hydrazones and oximes of 3-formylrifamycin SV.

The procedure of rifamycin derivatives preparation consists of condensation of 3-formylrifamycin SV with reactants suitable for carbonylic group, using solvents alone or in mixture, as reaction medium, in which are attained high concentrations of reactants, and from which the reaction products can be easily isolated, by possibly a partial concentration and/or water addition, when they separate under crystalline form.

The solvents and the working conditions selected, e.g. the reactant for carbonylic group in excess up to 0.25 mol, reduce the danger of inflammability, simplify the operations, decrease the degradations level and lead to pure products, so that their recrystallization is no longer necessary.

Among the obtained rifamycins, may be selected products showing reduced liver toxicity, active against mycobacteria rifamycin-resistant forms or specific antiviral-oncogene, immunosuppressive, antileukemic (in man) etc., activity utilizable in clinical use.

3 Claims, No Drawings

RIFAMYCINS AND METHOD FOR THEIR PREPARATION

This application is referring to new derivatives of 3-formyl rifamycin SV and to a method of theis preparation.

The known many semisynthetic rifamycins, but anly ane: 3-(4'-methyl-1'-piperasinyliminomethyl)-rifamycin SV known usually as rifampicin, is applied in therapy, exclusively as antimicrobial agent and especially in tuberculosis treatment.

As for as is known, the clinical use of rifamycin has shown a suite of deficiencies related to this substance. So it is liver, revealed during the prelonged tratment, due to a selective solubility of rifamycin in bile brings to an alteration of hepatic cell and rises the blood level of bilirubin. In the same time the relative quick rising of rifampicin resistance, restricts its uses in long duration therapy required by antituberculous treatments.

Furthermore, the experimental investigations performed during the last years demonstrated rifampicin shows a limitative potency reffering to antiviral, imunnosuppresive, antileukemic, effects, while other rifamycin derivatives exhibit much higher potencies regarding the above mentioned effects.

From the litterature are known many derivatives of 3-formylrifamycin SV, which have in the 3 position of the rifamycin SV ring a —CH=N—R group, where R may be a group

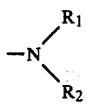

or a group —NH—CO—$R_3$ or a group —O—$R_4$ where $R_1$, $R_2$, $R_3$ and $R_4$ may be different alkilic, acylic, aralkilic groups of other possible substituted.

These rifamycins are performed by condensing 3-formylrifamycin SV with a nucleophyle reactant with aminic group, suitable for carbonylic group, general formula for nucleophilic reactant being I:

$$H_2N-R \qquad (I)$$

where R is as indicated above. (Romanian application No. 62,437; 62,778 and 62,882 U.S. patent application No. 3,342,810, French patent application No. 1,457,435; West German patent application Nos. 2,227,087 and 2,314,478. Journal of Medicinal Chemistry vol. 16 No. 10, pp. 1071-1075 (1973) and vol. 17, No. 9 pp. 948-953(1974)) all these procedures exhibit some disavantages.

Thus, using as reaction media tetrahydrofuran is disadvantageous for reasons of high inflammability, and due to isolation difficulties of final products.

Similarly, the use in some processes as reaction media of a single solvent, such as tetrahydrofuran benzene, ethyl acetate, chloroform or dioxan, in which one of the two reactants is very little soluble, leads to large volumes of reaction media.

Similarly, due to large solubility for the most part of 3-formylrifamycin SV derivatives in these solvents, in orider to isolate them is used an evaporation at sicc. and a recrystallization from other solvents, all these being difficult operations and also expensive, due to high solvent consumption and because it can nat be avoided unreacted carbonilic moieties.

Besides that, using the reactants in equimolar ratio that leads to an incomplete reaction, the end product being contaminated with 3-formylrifamycin SV.

The derivatives according to the present application avoid the above mentioned disadvantages and increase the range of semi-synthetic rifamycins having a chemical structure according to general formula II

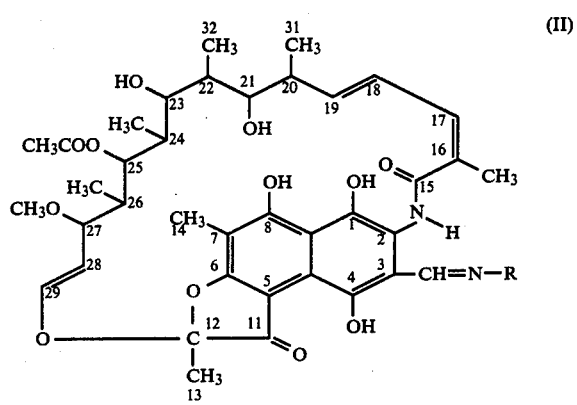

where R is

$R^1$ being a hydrogen atom and $R^2$—a radical of substituted arylpyridazine in aryl group with alkil groups or halide atoms, a benzthyazolile radical, a phenyl sulphonate radical, a phenyl radical substituted with au alkiloxy group or aryloxy nousubstituted or substituted, arylthio unsubstituted or substituted, or arylsulphonil; or $R^2$ is a piperidin radical substituted at N with alkilic or aralkilic groups; R may be —NH—CO—$R^3$ where $R^3$ is a phenyl substituted radical with nitre-, acylaminoand aminosulphonil groups, a heteroaromatic radical containing nitrogen, a phenoxyalkyl or phenoxyalkilden radical nonsubstituted or substituted in aromatic ring with a halide, alkyl, aminosulphonyl, alkylaminosulphonyl or dialkylaminosulphonyl, a benzhydril radical, lawere alcoxy or triazolomercaptomethyl substituted; R may be also —O—$R^4$ where $R^4$ is a halidealkyl radical; These derivatives are solid substances, crystalline, orange or red colored in different nuances, which generally decomposing at melting, very soluble in aliphatic hydrocarbons low halidic, soluble or slightly soluble in lower alkanols, ketones, aliphatic acids esthers with alkanols, aliphatic ethers, cyclic ethers, dimethylformamide, insoluble or very slightly soluble in aliphatic hydrocarbons and water; the method for thein preparation consists of condensing 3-formylrifamycin SV with a nucleophile reactant with au aminic group suitable for carbonylic group, general formula being I, which may be a hydrazine with general formula III or IV;

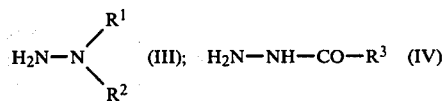

where $R^1$ an $R^2$ have the above mentioned signification or they are in independent way hydrogen atoms, alkyl groups with 1 to 20 carbon atoms, phenyl or benzyl, the arylic groups may be substituted with lower alkyl groups, nitro, carboxy, sulphamyl or with halide atoms; also $R^1$ and $R^2$ may build with nitrogen atom to which they are bond a heterocycle with 5 or 6 members with 1 or 2 nitrogen atoms; sometimes substituted with phenyl, benzyl or lower alkyl groups; $R^3$ has the same meanings specified above or it may be a phenyl radical amino, hydroxy, carboxyl, phenyl ar hydroxyphenyl groups; or it may be a hydroxyamine-O-substituted, with formula V:

$$H_2N-O-R^5 \qquad (V)$$

where $R^5$ is a hydrogen atom, an alkyl radical with 1–20 carbon atoms, eventually substituted with phenyl, carboxy, dialkylamino groups or halide, or an alkenyl radical with 2–20 carbon atoms; The procedure for preparing of rifamycins avoids the disadvantages of previons procedures known by the following:

3-formylrifamycin SV in crystalline form is directly brought into the reaction medium which contains the nucleophile reactant suitable for carbonylic group, or the 3-formylrifamycin SV is dissolved in high concentrations in solvent or solvents mixtures, or is suspended in the solvent and then the nucleophyle reactant solution is added;

in order to increase the reaction rate, to obtain more pure products and to reduce the dangers related to inflammability, as reaction medium are solvents used which belong to the lower aliphatic alchools with 1 to 5 carbon atoms, especially ethylic alchool, alone or in mixture with halogenated aliphatic hydrocarbons with 1–3 carbon atoms (especially dichloromethane) and in some cases water up to 10% from the solvent, volume used, medium where are attained high concentrations of the reactants;

in order to ensure the complete conversion of 3-formylrifamycin SV, the nucleophile reactant is used in a ratio of 1.05–1.25 mol to 1 mol of 3-formylrifamycin SV;

the condensing step is monitored at a temperature range between 5° C. and refluxing temperature of solvents until the total condensation of 3-formylrifamycin SV;

the nucleophile reactant may be used also as salt form, in such case is added an organic base in approximatively stoichiometric quantity;

the isolation of high purity reaction products is performed after their precipitation from the solvent system used, possibly modified through partial removal of one component or/and by water addition.

In the following pages 40 applicative examples are given.

EXAMPLE 1—3-3'-(p-toluil)-pyridazinyl-6'-hydrazonomethyl-rifamycin SV (reaction carried out in tetrahydrofuran):

Add to a solution of 758 mg 3-formyl-rifamycin SV, 96% purity, (1 mmol) in 20 ml tetrahydrofuran, at room temperature, a solution of 220 mg (1.1 mmol) 3-p-toluyl-6-hydrazinpyridazine in 10 ml tetrahydrofuran; after 20 minutes the chromatographic analysis shows the lack of 3-formylrifamycin SV; to concentrate under vacuum until 6 ml are reached; add 3 ml water in small portions under stirring; after 3 hours the crystaline product is filtered separately, which is rinsed with 60% ethanol, and dried;

Results 670 mg of product red-brick red colored; the yield is 75%.

Examined by thin-layer chromatography, the product shows no trace of 3-formylrifamycin.

Melting point: 219°–221° C. (decomposition); absorbtion maxima in U.V. and visible range at 355 nm ($E_1\ _{cm}^{1\%}=348$) and at 486 nm ($E_1\ _{cm}^{1\%}=175$).

In a parallel experiment performed with 200 mg hydrazine (1 mmol), the resulted product contains 3-formylrifamycin SV, that means it is contaminated with raw material.

EXAMPLE 2—3-3'-(p-toluyl)-pyridazinyl-6'-hydrazonomethyl-rifamycin SV (reaction in ethanol-dichloromethane):

Add to a solution of 758 mg 3-formylrifamycin SV 96% purity (1 mmol) in 4 ml mixture of ethanol-dichloromethane (1:1), at room temperature, a solution of 220 mg (1 mmol) 3-p-toluyl-6-hydazino-pyridazine in 8 ml mixture of ethanol-dichloromethane (1:1); after 15 minutes the chromatographic examination shows the reaction is completed; concentration until ⅓ of initial volume is reached, is induced the crystalization; after two hours is filtered, washed with ethanol and dried. Results 700 mg red coloured, crystaline product, without 3-formylrifamycin SV; The yield is 78%.

EXAMPLE 3—3-3'-(3",4"-dimethylphenyl)-pyridazinyl-6'-hydrazonomethyl-rifamycin SV.

To a solution of 257 mg (1.2 mmol) 3-(3',4'-dimethylphenil)-6-hydrazinpyridazine in 10 ml ethanol, heated at 45° C., are added 34 mg of 3-formylrifamycin SV, 99% purity, (1 mmol), under stirring; is kept 5 minutes at 45° C. when starts the crystalization; then is cooled down to 20° C. and after 2 hours is filtered.

The crystaline product is washed with ethanol and dried. Results 790 mg crystaline, dark red colored product; the yield is 85%.

The residual waters resulted from filtration, treated with 3 ml water yield 90 mg crystaline product, similar from chromatographic point of view with the main product; Overall yield is 95%.

A recrystalized sample from ethanol has melting point 200°–203° C. (with decomposition) and shows absorption maxima in U.V. and visible range at 356 nm ($E_1\ _{cm}^{1\%}=331$) and 487 nm ($E_1\ _{cm}^{1\%}=168$).

In parallel experiment performed with 235.5 mg (1.1 mmol) of hydrazinic compound, the final product contains 3-formyl-rifamycin SV.

EXAMPLE 4—3-3'(p-Chlorophenyl)-pyridazinyl-6'-hydrazonomethyl-rifamycin SV.

The working procedure is similar to that described in Example 3, using 265 mg (1.2 mmol) 3-p-chlorophenyl-6-hydrazinpyridazine; ane obtains 740 mg red cherry-brown colored product; the yield is 80%.

A recrystalized sample from ethanol has a melting point at 191°–203° C. (with decomposition) and shown absorption maxima in U.V. and visible range at 358 nm ($E_1\ _{cm}^{1\%}=337$) and 487 nm ($E_1\ _{cm}^{1\%}=168$).

EXAMPLE 5—3-3'-(p-isopropylphenyl)-pyridazinil-6'-hydrazonomethyl rifamycin SV.

The working procedure is similar to that described in Example 3, using 251 mg (1.1 mmol) of 3-p-isopropylphenyl-6-hydrazinopyridazine; are obtains 880 mg crystaline red brick colored product. The yield is 93%.

A recrystallized sample from ethanol has the melting point at 202°–205° C. and shows absorption maxima in U.V. and visible range at 358 nm ($E_1\ _{cm}^{1\%}=291$) and 487 nm ($E_1\ _{cm}^{1\%}=164.5$).

EXAMPLE 6—3-(Benzthiazolyl-2'-hydrazino-methyl)-rifamicin SV.

In 7 ml of ethanol are dissolved, in warm conditions, 173 mg (1.05 mmol) of benzthiazolyl-2-hydrazine; are added further 734 mg of 3-formylrifamycin SV 99% purity (1 mmol); after dissolution the reaction mass is kept 5 minutes at 40° C.; by subsequent stepwise addition of 1.5 ml water is separating the crystaline product; after a cooling down to room temperature and keeping alone for 1 hour is filtered, washed with some aqueous ethanol, and dried under vacuum; one obtains 720 mg of crystalline dark red cherry products; the yield is 82%.

The product has the melting temperature between 193°–197° C. (with decomposition) and shows absorption maxima in U.V. and visible range at 360 nm ($E_1\ _{cm}^{1\%}=291.5$) and 494 nm ($E_1\ _{cm}^{1\%}=179.5$).

EXAMPLE 7—3-(p-Butoxyphenylhydrazonomethyl)-rifamycin SV.

A solution prepared by solving 239 mg (1.1 mmol) of p-butoxyphenylhydrazine chlorhydrate and 0.08 ml pyridin in a mixture of 14 ml ethanol and 0.8 ml water, is added to a solution of 726 mg (1 mmol) 3-formylfiramycin SV in 2 ml dichloromethane and 2 ml ethanol; after keeping 15 minutes at room temperature one can observe the lack of carbonylic moiety; partially the dichloromethane is removed under vacuum, then is treated with 2 ml water; after 3 hours the crystalline precipitate is filtered. The precipitate is dark red cherry colored; to rinse with aqueous alchool, to dry under vacuum, and are obtains 600 mg product. The residual waters are diluted with 5 ml water and after 5 hours results 200 mg of additional product similar chromatographically with the main product. The yield is 90%.

The product, with melting temperature 148°–151° C. (with decomposition) and shows absorption maxima in U.V. and visible range at 321 nm ($E_1\ _{cm}^{1\%}=166$); 362 nm ($E_1\ _{cm}^{1\%}=147$) and 486 nm ($E_1\ _{cm}^{1\%}=172$).

EXAMPLE 8—3-(p-phenoxyphenylhydrazonomethyl)-rifamycin SV.

A solution prepared by solving of 248 mg (1.05 mmol) p-phenoxyphenylhydrazine and 0.08 ml pyridine in a mixture of 8 ml ethanol and 0.8 ml water, is added to a solution of 726 mg (1 mmol) 3-formylrifamycin SV in 2 ml dichlormethane and 2 ml ethanol; after 30 minutes at room temperature the chromatographie test shows the lack of carbonylic coresponnd; then the dichloromethane is partially removed under vacuum; after the starting of the crystallization is treated with 1.2 ml water; after 6 hours the product is recovered.

The crystalline product is dark red cherry.

Is rinsed then with aqueous alchool and rinsed under vacuum. One obtains 820 mg product. The yield is 90%.

The product has the melting point at 164°–168° C. (with decomposition) and shows absorption maxima in U.V. and visible range at 321 nm ($E_1\ _{cm}^{1\%}=165$), 370 nm ($E_1\ _{cm}^{1\%}=179$) and 486 nm ($E_1\ _{cm}^{1\%}=162$).

EXAMPLE 9—3-(phenoxyacetylhydrazobomethyl)-rifamycin SV (reaction in ethanol).

To a solution of 174 mg (1.05 mmol) phenoxyacethydrazide in 5 ml ethanol at approx. 40° C. is added under stirring 726 mg (1 mmol) 3-formylrifamycin SV; after few minutes starts the crystallization of the product; then is kept 3 hours at room temperature and filtered. Then is rinsed with alchool and dried. One obtains 810 mg of dark red colored product. The yield is 92%.

A recrystallized sample from ethanol has melting point at 160°–164° C. (with decomposition) and shows absorption maxima at 336 nm ($E_1\ _{cm}^{1\%}=290$) and 478 nm ($E_1\ _{cm}^{1\%}=164$).

EXAMPLE 10—3-(fenoxyacetylhydrazonomethyl)-rifamycin SV (reaction in dichloromethan-ethanol).

Dissolve 726 mg (1 mmol) of 3 formylrifamycin SV in 1.5 ml dichloromethan and dilute with au equal volume of ethanol. To the resulted solution is added a solution prepared by dissolving 174 mg (1.05 mmol) of phenoxyacethydraside in 6 ml ethanol at 35° C. After 25 minutes the chromatographie test reveals the lack of formylrifamycin. Then the dichloromethan is removed partially under vacuum. For crystalisation is added stepwise, under stirring, 2 ml water. For 2–3 hours the stirring is from time to time.

Filtrate and wash the crystaline dark red colored product twice with 0.5 ml aqueous alchool (75%).

After drying, one obtains 760 mg of product, identical chromatographycally and spectroscopically with the product obtained in Example 9. The yield is 87%.

In an experiment performed as described above, dissolving phenoxyacethydrazide in 12 ml ethanol and performing the reaction at 10° C., and using for precipitation 4 ml water, is observed by chromatography the lack of formylrifamycin after 45 minutes, and finally one obtains 700 mg product identical (from spectral and chromatographic point of view) with that obtained in example 9. The yield 80%.

EXAMPLE 11—3-(isonicotinoylhydrazinomethyl)-rifamycin SV (reaction in methanol).

To a solution of 151 mg (1.1 mmol) isonicotinichydrazide in 6 ml methanol at 45° is added 726 mg (1 mmol) 3-formylrifamycin SV, under stirring.

The mixture is kept 15 minutes, at 45°–50° C., when one can abserve the lack of formylrifamycin, and then cooled down slowly to room temperature.

The crystallization is improved by gradually addition of 1 ml water and stirring for 2 haours. Is filtered, then, the crystaline red colored product. The yield is 85%. A recrystallised sample from ethanol decomposes at 200°–205° C. and shows absorption maxima at 338 nm ($E_1\ _{cm}^{1\%}=287$) and 483 nm ($F_1\ _{cm}^{1\%}=166.5$).

Performing the condensation with an equimolar amount of hydrazide, one can observe chromatographically the presence in the reaction medium of the dimethylacetal of formylrifamycin which disappears when extra amounts of hydrazide.

EXAMPLE 12—3-(isonicotinoylhydrazonomethyl)-rifamycin SV (reaction in dichloromethan-ethanol).

To solve 726 mg (1 mmol) 3-formylrifamycin SV in 1.5 ml of dichloromethane and dilute with 1.5 ml ethanol.

Add to the resulted solution a solution prepared by solving of 151 mg (1.1 mmol) isonicotinic hydrazide in a mixture of 3 ml ethanol, 1 ml dichloromethane and 0.4 ml water. After keeping for 40 minutes at room temperature, the lack of formylrifamycin is revealed by chromatography. The dichloromethane is removed partially under vacuum when crystalisation starts. The crystallisation is completed by stepwise addition under stirring of 1.5 ml water (stirr 3 hours). Filter and rinse with aqueous alchool, then dry. Results 680 mg of product. The yield is 80%.

EXAMPLE 13—3-(nicotinoylhydrazonomethyl)-rifamycin SV.

The procedure is similar as in Example 11, using 144 mg (1.05 mmol) nicotinhydrazide solved in 15 ml methanol, and for completion of crystallisation are added 3 ml water. One obtains 680 mg crystaline, bright red colored product. The yield is 80%.

A recrystallized sample from dimethylformamido-ethanol-water has a melting point at 200°–204° C. (with decomposition) and shows absorption maxima at 338 nm ($E_{1\ cm}^{1\%}=285$) and 483 nm ($E_{1\ cm}^{1\%}=165$).

EXAMPLE 14—3-(p-chlorophenoxyacetylhydrazonomethyl)-rifamycin SV.

The workins procedure is similar to that described in Example 11. 210 mg (1.05 mmol) of p-chlorophenoxyacethydrazide dissolved in 10 ml of methanol and precipitate the product with water (2.5 ml).

One obtains 770 mg of crystalline, dark red colored product. The yield is 84%. Melting point is 156°–160° C. (with decomposition) and shows absorption maxima at 333 nm ($E_{1\ cm}^{1\%}=270$) and 486 nm ($E_{1\ cm}^{1\%}=152$).

EXAMPLE 15—3-(O-chlorophenoxyacetylhydrazonomethyl)-rifamycin SV.

The working procedure, similar to Example 9, using 210 mg (1.05 mmol) of O-chlorophenoxyacetylhydrazide. After cooling, the product precipitates in crystaline from by stepwise addition of 1.5 ml water.

A recrystallized sample from ethanol has melting point at 191°–193° C. (with decomposition) and shows absorption maxima at 335 nm ($E_{1\ cm}^{1\%}=277$) and 477 nm ($E_{1\ cm}^{1\%}=159$).

EXAMPLE 16—3-(O-chlor--phenoxypropionylhydrazonomethyl)-rifamycin SV.

A solution of 222 mg (1.05 mmol) O-chlor- -phenoxypropionyl hydrazide in 2 ml water at 40° C., is added to a suspension of 726 mg (1 mmol) 3-formylrifamycin SV in 10 ml ethanol.

Occurs the dissolution of formylrifamycin and from the purple colored solution, by cooling, needle form crystals, red-violet colored, are separating. After filtration, rinsing with aqueous ethanol and drying one obtains 660 mg of product. The yield is 71%. The recrystallized product from dichloromethan-ethanol decomposes at 205°–209° C. and shows absorption maxima at 337 nm ($E_{1\ cm}^{1\%}=244$) and 498 nm ($E_{1\ cm}^{1\%}=150$).

EXAMPLE 17—3-(2'-Methyl-4'-chlorophenoxyacetylhydrazonomethyl) rifamycin SV.

The working procedure is as in example 9, using 222 mg (1.05 mmol) o-methyl-p-chlorophenoxy-acethydrazide with stepwise addition of 1 ml water under stirring in order to precipitate the crystalline product. One obtains 780 mg of red-orange colored product. The yield is 85%.

A recrystallized sample from ethyl acetate-ethanol has shows absorption maxima at 335 nm ($F_{1\ cm}^{1\%}=260$) and 477 nm ($F_{1\ cm}^{1\%}=150$).

EXAMPLE 18—3-(o-chlorobenzoylhydrazonomethyl)-rifamycin SV.

The procedure of Example 9 was repeated using 179 mg (1.05 mmol) o-chlorobenzhydrazide dissolved in 5 ml ethanol at room temperature and adding the formyl-rifamycin SV at about 40° C. At cooling is separated microcrystalline product, hardly filtrable. After filtration, washing and drying results 720 mg of red-orange colored product. The yield is 82%.

The welting point is 175°–177° C. (with decomposition) and shows absorption maxima at 333 nm ($E_{1\ cm}^{1\%}=296$) and 478 nm ($E_{1\ cm}^{1\%}=171$).

EXAMPLE 19—3-(m-chlorobenzoylhydrazonomethyl) rifamycin SV.

The procedure of Example 18 was repeted using 179 mg (1.05 mmol) of m-chlorobenzhydrzide, and one obtains a red colored, crystalline product.

After filtration, washing and drying results 820 mg of product. The yield is 93%.

A recrystalised sample from ethanol-ethyl acetate has the melting point at 176°–180° C. and shows absorption maxima at 304 nm ($E_{1\ cm}^{1\%}=211$), 336 nm ($E_{1\ cm}^{1\%}=269$) and 483 nm ($E_{1\ cm}^{1\%}=148$).

EXAMPLE 20—3-(2'-hydroxy-4'-chlorobenzoylhydrazonomethyl)-rifamycin SV.

The procedure of Example 9 was repeated using 196 mg (1.05 mmol) of 4-chlorosalicylhydrazide dissolved in 10 ml ethanol.

Results 870 mg of bright-red colored, crystalline product. The yield is 97%.

A recrystallized sample from ethanol-ethylacetate decomposes at 196°–202° C. and shows absorption maxima at 304 nm ($E_{1\ cm}^{1\%}=220$), 345 nm ($E_{1\ cm}^{1\%}=278$) and 485 nm ($E_{1\ cm}^{1\%}=148$).

EXAMPLE 21—3-(carbetoxyhydrazonomethyl)-rifamycin SV.

The procedure of Example 9 was repeated, using 109 mg (1.05 mmol) of carbetoxyhidrazide and completing the crystallisation by addition of 2.5 ml water, and stirring for 3 hours. Results 630 mg of dark red colored crystalline product, The yield is 78%.

A recrystallized sample from aqueous alchool has melting point at 170°–174° C. (with decomposition) and shows absorption maxima at 334 nm ($E_{1\ cm}^{1\%}=280$) and 478 nm ($E_{1\ cm}^{1\%}=162$).

EXAMPLE 22—3-(2′-Bromethyloxyminomethyl)-rifamycin SV.

A solution of 232 mg (1.05 mmol) of O-(2-bromethyl)-hidroxilamine bromhydrate and 0.08 ml pyridin in 2 ml ethanol is added to a solution of 726 mg (1 mmol) of 3-formylrifamycin SV. The dichloromethane is removed under vacuum when the reaction product precipitates as crystalline form. After 1 hour is filtered, washed 3 times with 0.5 ml alchool and is dried under vacuum. One obtains 730 mg of red brick colored product. The yield is 86%.

The recrystallized product from ethanol has the melting point at 140°–148° C. and shows the absorption maxima in UV and visible range at 326 nm ($E_1$ $cm^{1\%}$ = 248) and 467 nm ($E_1$ $cm^{1\%}$ = 160).

EXAMPLE 23—The preparation of 3-(phenylhydrasonomethyl)-rifamycin SV.

To a solution of 132 mg (1.22 mmol) phenylhydrasine in 5 ml ethanol warmed to 50° C. are added under slow stirring 758 mg of 3-formylrifamycin SV (1 mmol) with 96% purity; the resulted solution is kept for 10 minutes in warm conditions. Thin layer chromatographie test on silicagel shows a complete condensation. Then the solution is cooled and are added drop by drop, under stirring, 4 ml water; the precipitated product is filtred, washed with 1 ml alchool 50% and dried. Results 660 mg of product, red-brick colored The yield is 80%. The product tested by thin layer chromatography shows the lack of 3-formylrifamycin SV.

An experiment performed with phenylhydrasine in a equimolar ratio led to a product containing 3-formylrifamycin SV.

Instead of ethanol used as solvent in this reaction may be used other alkanol with 1-5 carbon atoms.

EXAMPLE 24—Preparation of 3-(2′,4′-dinitrophenylhydrazonomethyl)-rifamycin SV.

To a solution of 218 mg (1.1 mmol) of 2,4-dinitrophenylhydrazine in 70 ml mixture of ethanol-dichloromethane (1:1 volumes) heated to 35° C., are added 758 mg of 3-formyl rifamycin SV, 96% purity, (1 mmol); the resulted red solution is kept 10 minutes in warm condition. The chromatographic test shows the lack of 3-formylrifamycin SV. The dichlormethane is removed by evaporation; the product crystallization is completed by stepwise addition of 25 ml water; stirr for 2 hours and filter the precipitated product. Wash with ethanol 60% and dry. One obtains 590 mg of dark red brown colored product (yield 65%).

Performing the condensation with dinitrophenylhydrazine in equimolar ratio, the resulted product contains 3-formylrifamycin SV, evidenced by chromatographie test.

Instead of dichlormethane as solvent may be used another aliphatic halogenated hydrocarbon with 1 to 3 carbon atoms.

EXAMPLE 25—Preparation of 3-(4′-Methyl-1′-piperasinylminomethyl)-rifamycin SV.

To a solution of 121 mg (1.05 mmol) of 1-amino-4-methylpiperasine in 5 ml ethanol, at room temperature, are added, under stirring, 758 mg of 3-formylrifamycin SV 96% purity (1 mmol). The obtained red-brick red colored solution is kept for 20 minutes, when the chromatographie test shows the lack of 3-formylrifamycin SV.

Dilute with 5-10 ml water and stirr; the dark-red colored crystalline product is filtered, washed with aqueous ethanol and dried.

Results 750 mg of product 99% pure (yield 90%).

Performing the reaction at +5° C., the chromatographie test (after 1 hour) shows the lack of 3-formylrifamycin SV, obtaining finally the product in the amount and purity above mentioned.

Performing the condensation with aminomethylpiperasine in equimolar ratio, the crystalline product contains 3-formyl rifamycin SV, observable by chromatographie test.

EXAMPLE 26—Preparation of 3-(4′-Methyl-1′-piperazinyliminomethyl)-rifamycin SV.

The procedure of Example 25 was repeated, using as reaction medium 5 ml methanol 95%, at 30° C. diluting finally the reaction medium with 3-5 ml water. One obtains finally 780 mg of product 99% pure (yield = 94%).

EXAMPLE 27—Preparation of 3-(phenylacetylhydrazonomethyl)-rifamycin SV (reaction in ethanol).

To a solution of 158 mg (1.05 mmol) phenylacethydrazido in 10 ml ethanol at 50° C. are added, under stirring, 758 mg 3-formylrifamycin SV, 96% pure (1 mmol). The dissolution is immediate and rapid and after 1 or 2 minutes starts the crystallization.

The solution is cooled, kept for 2 hours with stirring from time to time; the dark red crystalline product si filtred, then is washed with ethanol and dried under vacuum. Results 840 mg of product (yield is 98%).

EXAMPLE 28—Preparation of 3-(phenylacetylhydrazonomethyl)-rifamycin SV (reaction in methanol).

The procedure of Example 27 was repeated, using 165 mg (1.1 mmol) phenylacethydrazide, and as reaction medium 6 ml methanol. After the dissolution of formylrifamycin is refluxed for 15 minutes cooled and the crystallisation is completed by stepwise addition, under stirring, of 3 ml water. The heavy crystalline precipitate is filtred, washed with aqueous methanol and dried. Results 810 mg of product (yield 94%).

Chromatographically the product is similar with that obtained in Example 27.

EXAMPLE 29—Preparation of 3-(phenylacetylhydrazonomethyl)-rifamycin SV (reaction in ethanol-dichloromethane).

726 mg (1 mmol) of 3 formylrifamycin SV were dissolved in 1.5 ml dichloromethan the diluted with au equal volume of ethanol. To the resulted solution is added a solution prepared by dissolution of 158 mg (1.05 mmol) of phenylacethyldrazide in 6 ml ethanol at 35° C. After 25 minutes, the chromatographic test shows the lack of 3-formylrifamycin SV.

The dichlormethane is partially removed under vacuum, when strats the crystallization.

The crystallization is completed by stepwise addition of 1 ml water unde stirring. For 2 hours stirr form time to tine. Filter and wash the dark red colored crystalline product twice with 0.5 ml aqueous alchool (85%) each.

After drying results 815 mg of product (yield 94%).

One may work as above solving phenylacethydrazide in 15 ml ethanol at 10°–15° C. and monitoring the condensation reaction at 10° C.

In order to complete the crystallization are used 2 ml of water and one obtains 760 mg of product (yield is 87%).

EXAMPLE 30—Preparation of 3-(benzoylhydrazonomethyl)-rifamycin SV.

The procedure of Example 27 was repeated using 143 mg (1.05 mmol) of benzhydrazide. One obtains finally 760 mg of crystalline product (yield 91%).

EXAMPLE 31—Preparation of 3-(4-nitrobenzoylhydrazonomethyl) rifamycin SV.

The procedure of Example 28 was repeated using 190 mg (1.05 mmol) of p-nitrobenzhydrazide.

Finally, one obtains 820 mg of product (yield 93%).

EXAMPLE 32—Preparation of 3-(salicylhydrazonomethyl)-rifamycin SV.

The procedure of Example 27 was repeated, using 160 mg (1.05 mmol) of salicylhydrazide solved in 6 ml of ethanol. One obtains 830 mg of product (yield 96%).

EXAMPLE 33—Preparation of 3-(cyanoacetylhydrazonomethyl)rifamycin SV.

The procedure of Example 27 was repeated, using 104 mg (1.05 mmol) of cyanacethydrazide and completing the crystallization by addition of 2 ml water and stirring for 2 hours.

Results 720 mg of product. (yield 89%).

EXAMPLE 34—Preparation of 3-(carboxymethyloximinomethyl) rifamycin SV.

The procedure of Example 33 was repeated, using a solution of 120 mg (1.1 mmol) of O-carboxymethylhydraxilamine hemichlorhydrate in a mixture of 4 ml ethanol and 1.2 ml water. Results 740 mg of bright red colored crystalline product (yield 92%).

The product has the melting point at 194°–202° C. (with decomposition) and shows absorption maxima in UV and visible range at 326 nm ($E_{1\,cm}^{1\%}=265$) and 467 nm ($E_{1\,cm}^{1\%}=175$).

EXAMPLE 35—Preparation of 3-(benzyloximinomethyl)-rifamycin S.V.

The procedure of Example 33 was repeated, using a solution of 176 mg (1.1 mmol) O-benzylhydroxilaminehydrochloride and 0.08 ml pyridine in a mixture of 4 ml ethanol, 0.6 ml dichlormethan and 2 ml of water.

After 15 minutes the chromatographie test shows the into the respective oxime. After auether 10 minutes the crystallization begins 6 hours later, the crystalline product is filtred, washed with ethanol, and dreid. Results 760 mg of red colored product (yield 91%).

The recrystalised product from ethanol has a melting point of 150° C. (with decomposition) and shows absorption maxima in the UV and visible ranges at 327 nm ($E_{1\,cm}^{1\%}=261$) and 468 nm ($E_{1\,cm}^{1\%}=160$).

EXAMPLE 36—Preparation of 3-(oximinomethyl)-rifamycin SV.

In 1 ml of dichloromethane are dissolved 726 mg (1 mmol) of 3-formylsifamycin SV and is diluted with 2 ml of ethanol. Separately, 75 mg (1 mmol) of hydroxylamine hydrochloride are dissolved in 6 ml ethanol which also contains 0.08 ml of pyridin.

The solution of 3-formylrifamycin SV is added gradually, for 5 minutes into the hydroxylamino solution, under stirring, then wash the vessel 0.4 ml dichloromethan and 0.8 ml ethanol.

After 15 minutes at room temperature the chromatographis test shows the presence of the 3-formylrifamycin SV uncondensed. The crystallization begins and after about ½ hour allowed to stand at cold, the crystallization in completed. Filter, wash with ethanol and dry the product, 630 mg of red-orange (red-brick red) colored product are obtained. The yield is 85%. The product tested chromatographically shows no trace of 3-formylrifamycin SV.

The residual waters contain small quantities of 3-formylrifamycin together with the respective oxime of formylrifamycin SV.

Instead of dichloromethan may be used as the solvent another lower halogenated hydrocarbon.

EXAMPLE 37—Preparation of 3-(ethyloximinomethyl)-rifamycin SV.

A solution of 107 mg (1.1 mmol) of O-ethylhydroxylamine hydrochloride and 0.08 ml pyridin in 2 ml ethanol is added to a solution of 726 mg (1 mmol) of 3-formylrifamycin SV in 2 ml dichlormethan and 2 ml ethanol.

The chromatographie test, after 25 minutes, shows the lack of 3-formylrifamycin SV.

The dichlormethane is partially removed under vacuum when precipitates a red colored crystalline product.

The product is filtred, washed with 3 ml ethanol and dried under vacuum. Results 670 mg of product. The yield is 87%.

By the same procedure one obtains another alkyloximes, where the alkyl group has up to 20 carbon atoms.

EXAMPLE 38—Preparation of 3-(allyloximinomethyl)-rifamycin SV.

The procedure of example 37 was repeated, using 132 mg (1.2 mmol) of O-allylhydroxylamine hydrochloride. Results 675 mg of dark red colored crystalline product. The yield is 86%.

The residual waters are treated with 2 ml water under stirring and after filtration, washing and drying one obtains 80 mg of product similar chromatographically with the main product. Overall yield is 96%.

Similarly, one may obtain another alkemyloximes where the alkil group may have up to 20 carbon atoms.

EXAMPLE 39—Preparation of 3-(diphenylmethyloximinomethyl)rifamycin SV.

The procedure of example 37 was repeated, using 259 mg (1.1 mmol) of O-diphenylmethylhydroxylamine hydrochloride. After the removal of the dichloromethane the crystallization is completed by gradually addition of 2 ml water, under stirring.

Results 780 mg of red carmine colored crystalline product. The yield is 85.5%.

EXAMPLE 40—Preparation of 3-(octyloximinomethyl)-rifamycin SV.

The procedure of example 37 was repeated, using 249 ml (1.1 mmol) of O-acetylhydroxylamine hydrobromide. After the removal of the dichloromethan, are added 1.2 ml of water and is heated to 40° C., when the product previously separed changes into crystalline form.

One obtains 780 mg of red carmine colored crystalline product. The yield is 91%.

Other new rifamycin derivatives with general formula II are obtained by reacting the 3-formylrifamycin SV with the following nucleophilic reactants: 2-hydroxypropylhydrazine; 2-dimethylaminoethylhydrazine; 3-dimethylaminopropylhydrazine; 4-sulfophenylhydrazino; 4-(p-tolyloxy)-phenylhydrazine; 4-(phenylthio)-phenylhydrazine; 4-(p-tolylthio)-phenylhydrazine; 4-benzenesulfonylphenylhydrazine; 1-propyl-piperidin-4-il-hydrazine; 1-benzylpiperidin-4-il-hydrazine; 1-phenetylpiperidin-4-il-hydrazine; 4-acetylaminobenzhydrazide; 2,5-dihydroxybenzhydrazide; 2,4-dihydroxybenzhydrazide; 4-aminosulfonylbenzhydrazide; 3-nitrobenzhydrazide; 1-phenyl-2-benzyl-1,3,4-triazolyl-5-mercaptoacethydrazide, diphenylacethydrazide, O-butylhydorxylamine, O-isoamylhydroxylamine, O-isoamylhydroxylamine and O-(2-dimethylaminoacetyl)-hydraxylamine.

By the procedure presented in above mentioned examples it is possible to prepare other 3-formylrifamycin SV derivatives, by using a wide range of hydrazines substituted by a single nitrogen atom such as: 4-nitrophenylhydrazine, dimethylhydrazine; methylphenylhydrazine; diphenylhydrazine; phenylbenzylhydrazine; O-tolylhydrazine; p-tolylhydrazine; or aminooxyalkanes such as: o-vutylhydroxylamine; o-dodecylhydroxylamine; o-pentadecylhydroxyl amine; o-hexadecylhydroxylamine; o-actadecylhydroxylamine and o-phenylethylhydroxylamine.

By a similar procedure as in the Examples the others compounds represented by the formula II are prepared.

The new compounds of this invention have a very limited liver toxicity and are active against mycobacteria rifamycin resistant forms, or increase significantly the time of aquiring resistance, so permitting to be used in long duration treatments in antituberculosis therapy.

Also, some of these derivatives may be sebeted as products with specific antiviral - oncogenic, immunosupresive, antilaenkemic (human) etc. activities, for clinical use.

From the above mentioned examples, results the superiority of the procedure according to this application versus already known procedures. So, the solvent systems used, permit to obtain high concentrations of reactants at room temperature thus enhanming the reaction rates. Thus the yields are also increased and the possible side reactions due to heating are avvided.

Thus, in dichlormethan - ethanol system, the formylrifamycin is soluble 250 mg per ml.

In addition, using as reactant the crystalline form of 3-formylrifamycin reduces the solvent volume used, ensuring thus a higher reactants concentration and consequently au appreciable rising of reaction rate.

Also, the selected solvents ensure a simple and advantageous preparation of end products, the last ones being hardly soluble even in the reaction medium or after the partial removal of the halogenated hydrocarbon or passibly by water addition.

These facts are based ou the statement that the rifamycin derivatives are generally soluble on very soluble in halogenated hydrocarbons and hardly soluble in water. The alchool is used both to ensure the solubilisation of reactant for carbonylic group and to allow the creation of a ternar solvent system with water.

The exceeding nucleophile reactant ensures the quantitative condensation of 3-formylrifamycin SV, which contributes to obtaining high purity products.

Avoiding of such well known operations such as: evaporation to sice, of reaction medium and the recrystallization (when arise conditions for partial degradation) contributes also to obtain high purity products.

The procedure, according to this application presents the following advantages:

enables to operate with small volumes and safely by using, as reaction medium, of solvents with a low degree of danger but with a high degree of solubilization of reactants and by solubilization of 3-formyl rifamycin SV directly in the reaction medium, where is present the nucleofile reactant;

increases the reaction rate and the solubility of reactants by performing the operations at higher temperatures than the room temperature;

enables the easy isolation of the end products with high yields and high purities by dilution with water on after removal of one of the solvents.

ensures the lack of other rifamycins (for instance: 3-formylrifamycin SV) in end products, by using of an excess of nucleofile reactant.

We claim:

1. A compound of the formula:

[structural formula of rifamycin derivative with CH=N—R substituent]

wherein R is $$-N\begin{matrix}R_1\\R_2\end{matrix}$$

wherein
   $R^1$ is hydrogen; and
   $R^2$ is phenylpyridazinyl with the phenyl substituted with a 1 to 3 carbon alkyl group or a halogen atom.

2. The compound defined in claim 1 selected from the group consisting of:

3-3'-(p-toluyl)-pyridazinyl-6'-hydrazonomethyl-rifamycin SV;

3-3-(3'',4''-dimethylphenyl)-pyridazinyl-6'-hydrazonomethyl-rifamycin SV;

3-3'-(p-chlorophenyl)-pyridazinyl-6'-hydroazonomethyl-rifamycin SV; and 3-3'-(p-isopropylphenyl)-pyridazinyl-6'-hydrazonomethyl-rifamycin SV.

3. In a process for preparing a compound of the formula:

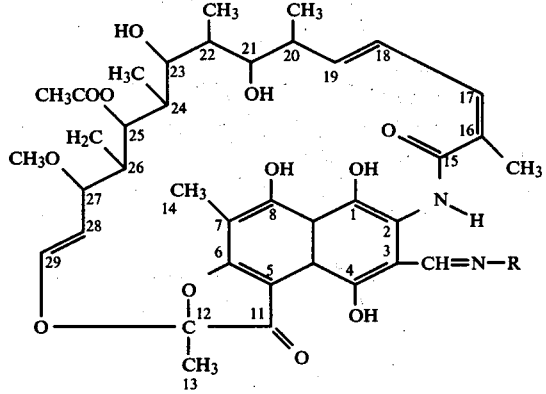

wherein R is

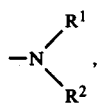

wherein
R¹ is a hydrogen atom, and
R² is selected from phenylpyridazinyl with the phenyl substituted with a 1 to 3 carbon alkyl group or a halogen atom; benzthiazolyl; phenyl substituted with a 1 to 4 carbon alkoxy group or an unsubstituted phenoxy group or halogen substituted phenoxy group; phenylthio unsubstituted or substituted with a methyl or methoxy group; piperidinyl N-substituted with a 1 to 8 carbon alkyl group, or substituted with a phenyl or benzyl group; or R is —NH—CO—R³, wherein R³ is selected from phenyl substituted with nitro groups, acetylamino or aminosulphonyl groups; pyridazino, substituted pyridazino, pyridyl; phenoxyalkyl with 1 to 2 carbon alkyl; unsubstituted or substituted in the aromatic moiety with halogen, methyl, aminosulphonyl or hydroxyl; benzhydryl; or 1-phenyl-2-benzyl-1,3,4-triazolyl-5-mercaptomethyl; or R is —O—R⁴, wherein R⁴ is 2-bromethyl; carboxymethyl; or benzyl; prepared by reaction in a suitable reaction medium of 3-formylrifamycin SV with a nucleophilic reactant with an —NH₂ group which has one of the following formulae:

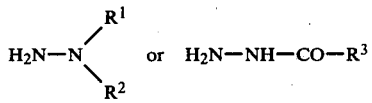

wherein R¹ and R² are as defined above or they are independently hydrogen atoms, alkyl groups with 1 to 20 carbon atoms, phenyl, benzyl, phenyl or benzyl substituted by lower alkyl, nitro, carboxy, sulfonyl, or halo; or R¹ and R² form together a pyridyl, pyridazino, or pyridazino group substituted by phenyl, benzyl or lower alkyl;

R³ is as defined above or is phenyl or phenyl substituted by halo, nitro, hydroxy, or amino; or R³ is phenylalkyl where the alkyl has 1 to 5 carbon atoms where the alkyl is unsubstituted or substituted by cyano, amino, hydroxy, carboxy, phenyl or hydroxyphenyl; or prepared by reaction of a nucleophilic reactant with an —NH₂ group of the following formula:

H₂N—O—R⁵ wherein R⁵ is hydrogen, alkyl with 1 to 20 carbon atoms, unsubstituted or substituted phenyl, carboxy, dialkylamino, or halo; or R⁵ is alkenyl with 2 to 20 carbon atoms; wherein the improvement comprises:

introducing the 3-formylrifamycin SV into the reaction medium at high concentrations or suspending the 3-formylrifamycin in the reaction medium followed by the addition of the nucleophilic reactant wherein the reaction medium contains an aliphatic alcohol with 1 to 5 carbon atoms alone or in admixture with an aliphatic halohydrocarbon with 1 to 3 carbon atoms.

* * * * *